United States Patent [19]

Ogino

[11] Patent Number: 5,436,717
[45] Date of Patent: Jul. 25, 1995

[54] APPARATUS FOR ANALYZING PARTICLES

[75] Inventor: Shinichi Ogino, Kobe, Japan

[73] Assignee: Toa Medical Electronics Co., Ltd., Kobe, Japan

[21] Appl. No.: 31,498

[22] Filed: Mar. 15, 1993

[30] Foreign Application Priority Data

Apr. 1, 1992 [JP] Japan .................. 4-108827

[51] Int. Cl.$^6$ .................. G01N 33/48; G01N 15/14
[52] U.S. Cl. .................. 356/72; 356/73; 250/458.1; 250/461.2
[58] Field of Search .................. 358/72, 73, 317, 318, 358/417; 250/458.1, 459.1, 461.1, 461.2

[56] References Cited

U.S. PATENT DOCUMENTS

| 4,609,286 | 9/1986 | Sage, Jr. ........................ 356/73 |
| 4,643,566 | 2/1987 | Ohe et al. ...................... 356/72 |
| 4,957,363 | 9/1990 | Takeda et al. .................. 356/73 |
| 5,050,987 | 9/1991 | Kosaka .......................... 356/73 |
| 5,159,398 | 10/1992 | Maekawa et al. ................ 356/73 |
| 5,260,764 | 11/1993 | Fukuda et al. .................. 356/73 |
| 5,272,354 | 12/1993 | Kosaka .......................... 356/336 |

Primary Examiner—William Mintel
Assistant Examiner—Minhloan Tran
Attorney, Agent, or Firm—Jones, Tullar & Cooper

[57] ABSTRACT

An apparatus for analyzing particles capable of irradiating uniform fluorescent excitation light efficiently, without difficulty in position adjustment, to a flat sample liquid flow containing particle components such as blood and urine, and capable of measuring side fluorescence or scattered light. By irradiating a sample liquid flat flow with fluorescent excitation light by a light source from the narrower side of a sample liquid flat flow, the fluorescence emitted from the broader side of the sample liquid flat flow is detected by a photo detector, and the signals from this photo detector are entered in a signal processor to be processed.

5 Claims, 7 Drawing Sheets

A
APPARATUS FOR ANALYZING PARTICLES

BACKGROUND OF THE INVENTION

The present invention relates to an apparatus for analyzing particles by passing a sample liquid containing particle components such as blood and urine in a sheath flow, irradiating light to the sample liquid flow, detecting the light from the particles, and analyzing the particles, and more particularly to an apparatus for analyzing particles capable of obtaining intense fluorescence without variance (dispersion) among particles, by irradiating the sample liquid flowing in a flat flow with a uniform and intense fluorescent excitation (excited) light. The sheath flow is a flow which covers the suspension of particles with a laminar sheath liquid in order to pass the particles by aligning them in one row precisely in the middle of the liquid flow. As the sheath liquid, usually, a diluent liquid or the like is used.

There is conventionally an apparatus for classifying and counting particles by irradiating particles with a fluorescent excitation light such as dyed cells, and detecting the fluorescence emitted from the particles. An example thereof is a flow cytometer. In the flow cytometer, in order to increase the number of particles to be analyzed, the sample liquid flow is passed in a broad (wide) flow in one direction, instead of a columnar flow. As disclosed in Published Japanese Laid-open Patent Sho. 57-500995 (which corresponds with U.S. Pat. No. 4,338,024), the sample flow containing particles is flattened to a flat flow, and still pictures of particles are taken by a strobe light and video camera.

In the flow cytometer, it is necessary to irradiate the flowing region of the sample liquid with a uniform light. When the sample liquid flow is a flat flow, as shown in FIG. 1, light 102 from a laser light source 100 is formed into an elliptical light by using cylinder lens or prism 104, and irradiating the sample flow 106 from the front (the broader side of the flat flow), so that the light intensity may be uniform.

However, the light intensity distribution emitted from the laser light source has a Gaussian distribution, and if, for example, an elliptical spot of 10×300 μm is formed, the actual uniform range of light intensity is only 20 to 30 μm in the central part thereof. Accordingly, if it is desired to have a uniform light intensity in a measuring region of about 150 μm in width of a sample flat flow, the major diameter (axis) of the ellipse must be considerably longer, namely, several millimeters. When the major diameter of the ellipse is longer, the excitation light intensity per unit area becomes smaller, and the obtained fluorescence is feeble, and is hard to detect.

Besides, by irradiating the front of the flat flow by fluorescent excitation light, it is impossible to detect the side scattered light or side fluorescence from the side surface (the narrower side of the flat flow), and it is impossible to adjust the focus in the entire measuring region.

The art for making the irradiation light intensity uniform was disclosed in (a) Published Japanese Laid-open Patent Hei. 3-200051, and (b) Published Japanese Laid-open Patent Hei. 2-304333.

In (a), the irradiated light is reflected by a corner cube prism to form a plurality of parallel laser beam rows. The light is made uniform by overlapping parts of the incident light and reflected light. In (b), a light concentration (density) plate low in transmissivity in its middle portion and high on its sides is used to produce a uniform light intensity.

However, in (a), the light must be reflected continuously within the same plane, and it is difficult to adjust the prism position, which is not practical.

In (b), it is difficult to manufacture a light concentration plate having uniform characteristics, and it is also hard to adjust the position of the light concentration plate. Besides, the light is attenuated (damped).

OBJECT AND SUMMARY OF THE INVENTION

It is hence a primary object of the present invention to provide an apparatus for analyzing particles capable of irradiating uniform light in a flat sample liquid flow efficiently without any difficult in position adjustment.

To achieve the above object, the present invention is constructed as shown in FIG. 2, in which a flattened sample liquid flow 14 is irradiated with light from the narrower side of the flow, and the light intensity distribution within the detecting region is made uniform. Numeral 10 is a light source, and 12 is a condenser lens.

Generally, when the laser light is focused (condensed) by the lens, the luminous flux (beam becomes as shown in FIG. 3, that is, there is a region called a beam waist 17 nearly unchanged in diameter of the luminous flux before and after the focal position of the lens.

Therefore, by properly setting the focal length of the condenser lens 12 and the luminous flux diameter of the incident light, a beam waist longer than the measuring region is formed. As a result, the spatial intensity distribution becomes uniform in the direction of the optical axis, and a laser luminous flux having a Gaussian distribution in the direction vertical to the optical axis is formed. Thus, the intensity distribution of light of the entire light in the measuring region may be kept constant.

For example, supposing the detecting region to be 150×15 μm by using an Ar (argon) laser as the light source, the spot diameter (2w) when focusing the laser light by a lens is expressed as follows, defining the focal distance of the lens to be f, the diameter of luminous flux of the incident light to the lens to be 2W, and the wavelength of light to be λ.

$$2w = 2\,(4\lambda f/3\pi W)$$

At a position remote from the focal position of the lens by a distance z, the diameter of luminous flux 2w' is expressed as follows.

$$2w'(z) = 2w[1+(\lambda z/\pi w^2)^2]^{\frac{1}{2}}$$

Allowing the diameter of luminous flux to be 5% larger, it is approximated as follows.
$$z = 0.32\pi w^2/\lambda$$

Using, as the light source, an Ar laser having an output wavelength of λ=488 nm and an exit luminous flux diameter 2W=1.0 mm, and using a lens with a focal length f=19 mm as the condenser lens, a luminous flux diameter of 2w=approx. 15.7 μm and a beam waist of z=approx. 300 μm are obtained at the focal position, so that the measuring region of 150 μm may be sufficiently covered. At this time, at both ends of the detecting region, the luminous flux diameter is about φ16 μm, and it is only about 1.7% larger against the diameter of the focal position, and the light intensity per unit area may be regarded almost unchanged.

Furthermore, since the diameter of luminous flux can be set at φ15.7 μm, the light intensity per unit area may be more than 100 times greater as compared with the prior art.

Besides, supposing the thickness of the sample flow to be 10 μm, it is necessary to make the intensity uniform to a certain extent in the direction vertical to the direction of the optical axis in consideration of the stability of the sheath flow.

Accordingly, if an elliptical luminous flux is formed by inserting a light forming element, the peak value of the luminous intensity in the direction of the optical axis is not changed. In this case, the flatness of the luminous flux is about 15.7×200 μm, and the luminous intensity per unit area may be nearly the same as in the prior art.

The apparatus for analyzing particles of the present invention is, for example as shown in FIG. 4, an apparatus for enveloping (covering) a sample liquid containing particles with a sheath liquid and passed to form a sheath flow, and irradiating light to the sample liquid flow to detect particles, wherein

- a sample liquid flow 14 is a flat flow narrow in one direction and broad (wide) in the another direction, comprising:
- a light source 10 for irradiating a sample liquid flat flow with light (fluorescent excitation light) from the narrower side of the sample liquid flat flow 14,
- a photo detector 38 for detecting the light (fluorescence) emitted from the broader side of the sample liquid flat flow 14, and
- a signal processor 40 for receiving and processing the signal from the photo detector 38.

In the apparatus of the present invention, as shown in FIG. 2, the light (fluorescent excitation light) is reduced (narrowed down) and irradiated to the narrower side of the flat sample liquid flow 14. The irradiated light (fluorescent excitation light) directly passes through the sample liquid flat flow 14 longitudinally. Therefore, in the irradiated region of the light (fluorescent excitation light) of the sample liquid flat flow, the light (fluorescent excitation light) intensity is almost uniform. Besides, of the irradiated light, the light irradiated outside of the sample liquid flow is slight, and hence the sample liquid flow can have a stronger light (fluorescent excitation light) irradiated to it.

The light (fluorescent excitation light) from the particles is detected from the broader side of the flat flow. Since the sample liquid flow in that direction is narrow, it is easy to adjust the focus.

Another apparatus of the present invention is, as shown in FIG. 4, an apparatus for enveloping a sample liquid containing particles with a sheath liquid, passed to form a sheath flow, and irradiating the sample liquid flow with light to detect particles, wherein

- a sample liquid flow 14 is a flat flow narrow in one direction and broad (wide) in the another direction, comprising:
- a first light source 10 for irradiating the sample liquid flat flow with first light (fluorescent excitation light) from the narrower side of the sample liquid flat flow 14,
- a photo detector 38 for detecting the light (fluorescence) emitted from the broader side of the sample liquid flat flow 14 by the irradiation of the first light,
- a second light source 18 for irradiating the sample liquid flat flow with second light (illumination light) from the broader side of the sample liquid flat flow 14,
- a one-dimensional image sensor 36 for imaging the transmitted light images or scattered light images by the second light (illumination light) passing through the sample liquid flat flow 14, and
- a signal processor 40 for receiving and processing the signals from the photo detector 38 and the one-dimensional image sensor 36.

Another apparatus of the present invention is, as shown in FIG. 8, an apparatus for enveloping a sample liquid containing particles with a sheath liquid, passed to form a sheath flow, and irradiating the sample liquid flow with light to detect particles, wherein

- a sample liquid flow 14 is a flat flow narrow in one direction and broad in the another direction, comprising:
- a first light source 10 for irradiating the sample liquid flat flow with first light (fluorescent excitation light) from the narrower side of the sample liquid flat flow 14,
- a photo detector 38 for detecting the light (fluorescence) emitted from the broader side of the sample liquid flat flow 14 by the irradiation of the first light,
- a second light source 18 for irradiating the sample liquid flat flow with second light (illumination light) from the broader side of the sample liquid flat flow 14,
- a one-dimensional image sensor 36 for imaging the transmitted light or scattered light by the second light (illumination light) passing through the sample liquid flat flow 14,
- a third light source 42 for irradiating the sample liquid flat flow with pulse light from the broader side of the sample liquid flat flow 14,
- a two-dimensional image sensor 50 for picking up particle images by the third light passing through the sample liquid flat flow 14, and
- a signal processor 52 for receiving and processing the signals from the photo detector 38, the one-dimensional image sensor 36, and the two-dimensional image sensor 50.

The signal processor 52 possesses the function of radiating the third light source on the basis of the signal from the one-dimensional image sensor 36, that is, the particles are detected, and particle images are picked up.

BRIEF DESCRIPTION F THE DRAWINGS

Figure 1:
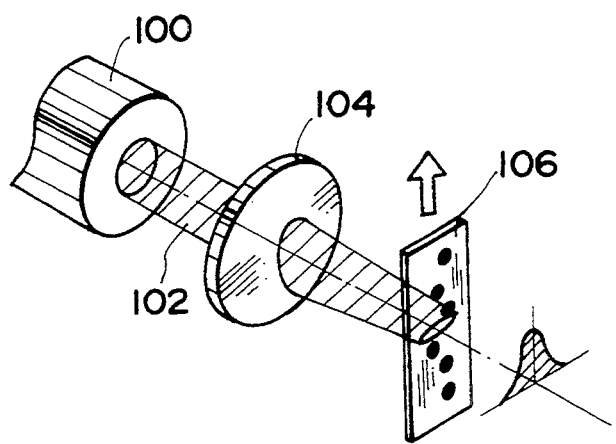
FIG. 1 is a perspective view for explaining the measuring principle in a conventional apparatus for analyzing particles.
Figure 2:
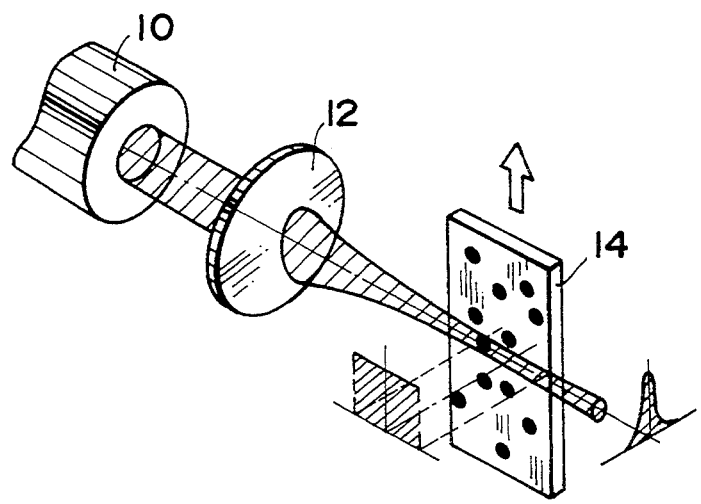
FIG. 2 is a perspective view for explaining the measuring principle in a apparatus for analyzing particles of the present invention.
Figure 3:
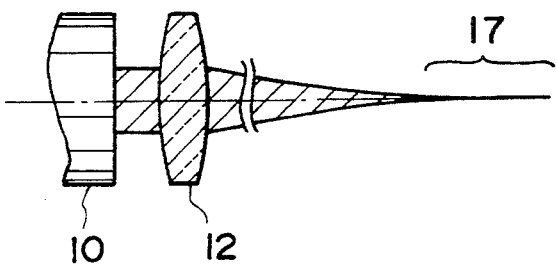

FIG. 3 sa general explanatory diagram showing the state of a luminous flux by condensing the laser light by a lens.

Figure 4:
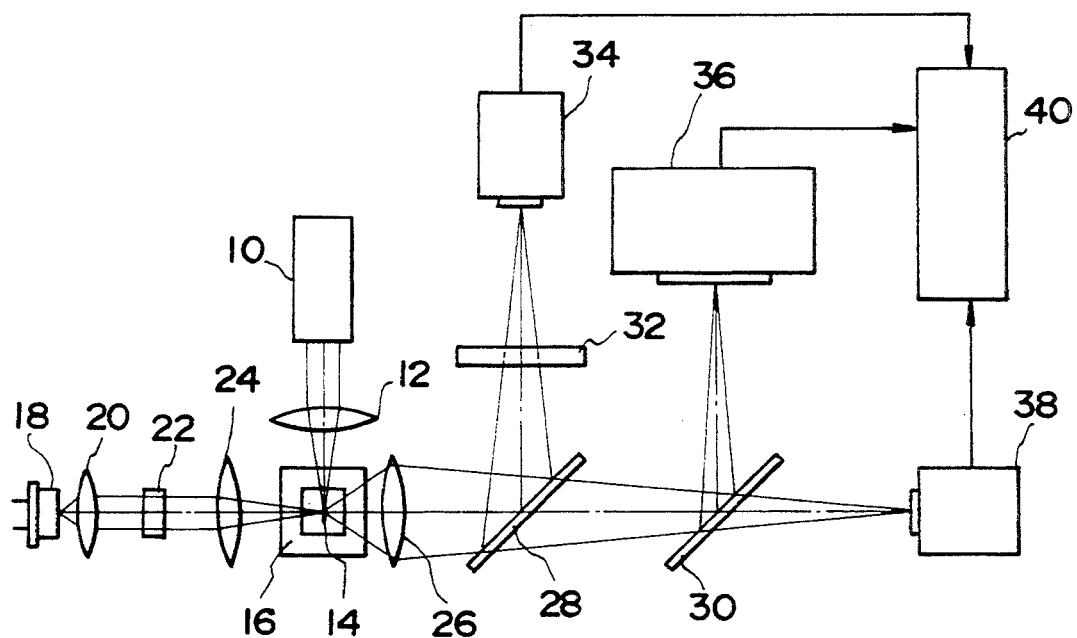

FIG. 4 is a schematic diagram showing an embodiment of an apparatus for analyzing particles of the present invention.

Figure 5:
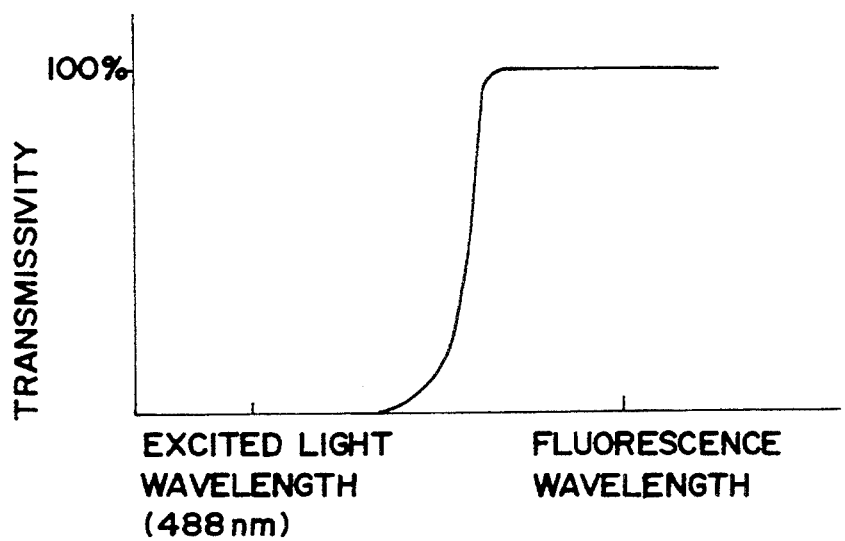

FIG. 5 is a characteristic diagram of a first dichroic mirror in FIG. 4.

Figure 6:
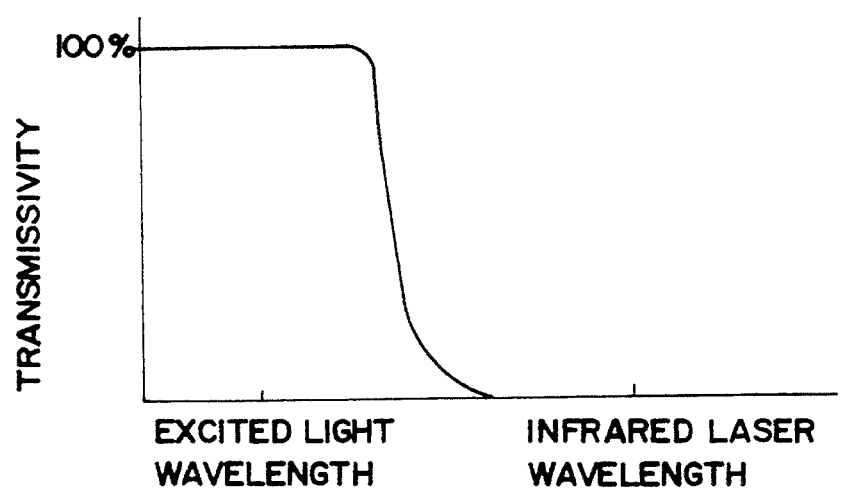

FIG. 6 is a characteristic diagram of a filter in FIG. 4.

Figure 7:
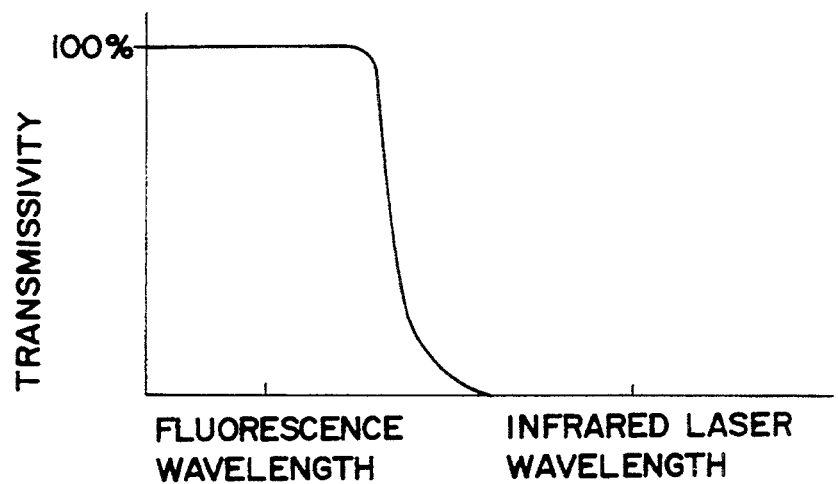

FIG. 7 is a characteristic diagram of a second dichroic mirror in FIG. 4.

Figure 8:
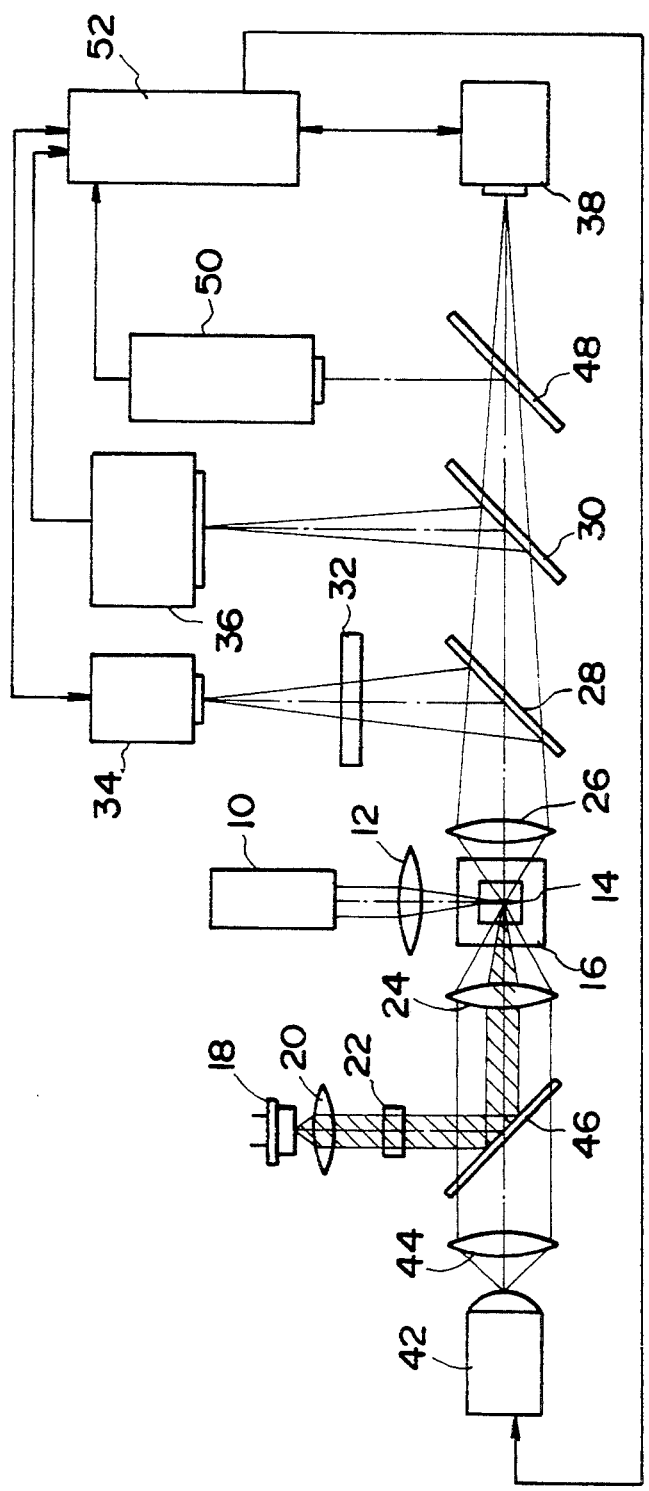

FIG. 8 is a schematic diagram showing another embodiment of an apparatus for analyzing particles of the present invention.

Figure 9:
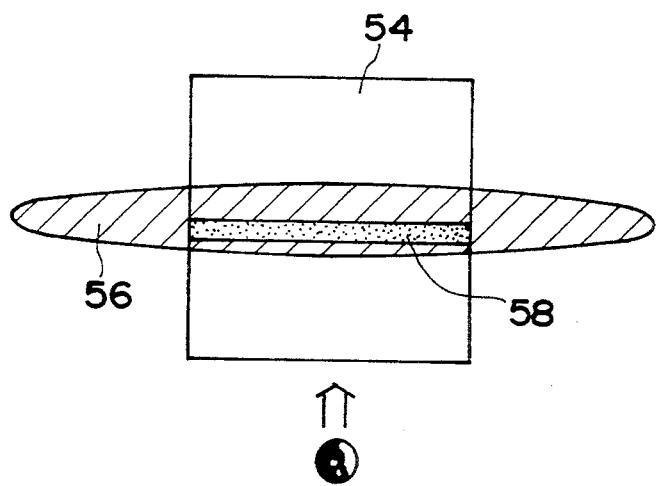

FIG. 9 is an explanatory diagram showing a line sensor image pickup region, a video camera image pickup region, and an excitation light irradiation region in a flow cell unit shown in FIG. 8.

Figure 10:
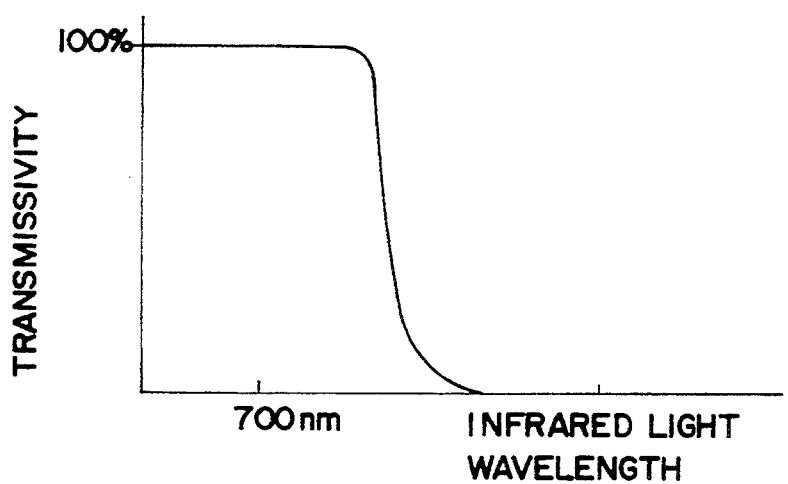

FIG. 10 is a characteristic diagram of a third dichroic mirror in FIG. 8.

DETAILED DESCRIPTION OF THE PREFERRED EMBODIMENTS

Referring now to the drawings, some of the preferred embodiments of the invention are described in detail below.

Embodiment 1

FIG. 4 is a schematic diagram of the apparatus of the embodiment. As a pretreatment, the diluted and dyed sample is led into a flow cell 16 to form a sheath flow by sheath liquid, and a flat sample flow 14 flows in the flow cell 16. The flow cell 16 is constructed of a transparent body such as glass or plastic, and comprises a lead-in passage gradually narrowed in width in one direction only, a narrow measurement passage connected to this lead-in passage, a sheath liquid feeding port provided in the lead-in passage, and a discharge port provided downstream of the measurement passage.

A light source 10 for excitation is a laser light source, and, when measuring fluorescent dyed particles, a light source of optimum excitation wavelength, such as an Ar laser, a dye laser, and a He—Cd laser is selected depending on the fluorescent dye. An example of an Ar laser is described below.

A condenser lens 12 is provided for irradiating illumination light to the sample flow in the flow cell 16. A light receiving lens 26 for condensing the fluorescence and side scattered light emitted from the particle passing the irradiation region of excitation (excited) light. A first dichroic mirror 28 for passing the fluorescence from the particles and reflecting the side scattered light, and it possesses the waveform characteristic as shown in FIG. 5.

An infrared light cut-off filter 32 possessing the characteristic shown in FIG. 6 is intended to remove the infrared light leaking out of the first dichroic mirror 28, from the infrared light emitted from a light source 18 for illuminating particles.

A photo detector 38 detects the fluorescence passing through the first dichroic mirror 28 and the second dichroic mirror 30. A photo detector 34 detects the side scattered light reflected by the first dichroic mirror 28. An example of the characteristics of the second dichroic mirror 30 is shown in FIG. 7.

The light source 18 for illuminating particles is a light source which emits light in the infrared region, and is, for example, a laser diode for emitting near infrared light. The light emitted from this light source is transformed into parallel light in a collimator lens 20, is shaped by a light shaping element 22 such as a prism or a cylinder lens, and is condensed by the condenser lens 24 so as to form a long elliptical spot of, for example, $20 \times 500$ $\mu$m, in the sample flow in the flow cell 16.

The light passing through the sample liquid flow 14 is condensed by the light receiving lens 26, passes through the first dichroic mirror 28, is reflected by the second dichroic mirror 30, and is imaged in a line sensor (one-dimensional image sensor) 36.

At this time, the arrangement is such that the excitation light from the excitation light source 10 and the illumination light from the illumination light source 18 may cross in the detecting region in the flow cell.

As the particle passes through the long elliptical measuring region, the transmitted light image of the particle is formed on the line sensor (one-dimensional image sensor) 36, and it is noted that the particle has passed because the quantity of light entering each pixel (picture element) varies. At the same time, the intensity of the side scattered light by the Ar laser is detected by the photo detector 34 and is measured, and when the particle has been dyed with fluorescence, the fluorescence intensity is measured by the photo detector 38.

Afterwards, the signals from the photo detectors 34 and 38, and line sensor 36 are processed in a signal processor 40.

Next, particle detection by the line sensor 36 will be explained. As mentioned above, when a particle passes the illuminated spot, the quantity of incident light to the pixel in the portion corresponding to the particle image on the line sensor 36 varies, as a result, a signal corresponding to the exposure quantity of each pixel of the focused particle image is produced. By processing this signal, the size of the particle and other information may be acquired.

For example, using a CCD element, the size of one pixel is $13 \times 13$ $\mu$m, the number of pixels is 256, the clock is 10 MHz as the line sensor, a 20-times objective lens as the light receiving lens 26 is used, the measuring region in the flow cell 16 of the line sensor 36 is about $0.65 \times 166$ $\mu$m, and 20 $\mu$sec is taken for producing signals for all pixels of the CCD.

Assuming the flow velocity of a sample flow to be 100 mm/sec, a particle moves by 2 $\mu$m in 20 $\mu$sec, and if the size of the particle is $\phi 10$ $\mu$m, five corresponding signals are obtained for one particle.

By analyzing the signals in the signal processor 40, the particle size, area, and other morphological information are obtained. For this signal processing method, patents have been applied for in Japan as Japanese Patent Applications Hei. 3-270106 and Hei. 3-270107.

In addition, by the signal processing, it can be detected whether several particles have passed simultaneously within the detecting region, and processing is possible at this time, without requiring data of fluorescence or side scattered signals detected in the photo detectors 38, 34.

In this way, morphological information, fluorescent intensity, and side scatter intensity of the particles passing through the detecting region are measured.

Furthermore, when the morphological information of the particle is not measured, the width of the detecting region may be set at about 90 $\mu$m, the image magnification of light receiving lens 26 may be 20 times, and a CCD element may be used with a pixel size of $14 \times 14$ $\mu$m, the number of pixels at 128, a clock at 60 MHz used as the line sensor 36, a measuring region in the flow cell 16 of the line sensor 36 of about $1.4 \times 90$ $\mu$m, and a requirement of about 2 $\mu$sec for producing signals for all pixels of the CCD. Supposing the velocity of a sample flow to be 5 m/sec, the moving distance of a particle in one signal reading time is 10 $\mu$m, and the shape parameters such as particle area cannot be measured, but the particle size can be measured. In this case, the diameter of the sample liquid flow is 6 times as compared with $\phi 15$ $\mu$m of the conventional flow cytometer apparatus, the sample liquid flow velocity is equal, and therefore the number of cells analyzed per unit time is six times more than in the flow cytometer apparatus. Actually, considering the presence of simultaneous passing of particles by about 7%, the number of cells that can be analyzed is about 5.5 times more.

Embodiment 2

FIG. 8 is a schematic diagram of an apparatus of this embodiment. In this embodiment, an image pickup system for obtaining particle images and an image processor are added to the apparatus of Embodiment 1.

The information obtained in the apparatus in Embodiment 2 is analyzed in real time, and when the passing particle is judged to be the object particle, a strobe light source 42 emits light one moment, and white light is irradiated to the particle, so that the particle image is picked up by a video camera (two-dimensional image sensor) 50.

The white light emitted from the strobe light source 42 passes through a third dichroic mirror 46, is condensed by the condenser lens 24, and irradiates the flow cell 16. The light passing through the particle runs through a light receiving lens 26, first dichroic mirror 28, and second dichroic mirror 30, is reflected by a half mirror 48, and is imaged on the CCD surface of the video camera 50.

Herein, when the strobe light source 42 emits light, for example, a photomultiplier with a gate function is sued so that the strobe light may not enter the photo detectors 38, 34 (that is, the gate is applied so that the photomultiplier may not function while the strobe is emitting light).

FIG. 9 shows a line sensor image pickup region 58, a video camera image pickup region 54, and an excitation light irradiation region 56. FIG. 10 shows a characteristic example of the third dichroic mirror 46.

As mentioned above, the signal from the line sensor is analyzed in real time, and supposing the analysis time to be 100 μsec and the sample flow velocity to be 100 mm/sec, the moving distance of the particle within the analysis time is 10 μm. Therefore, by disposing the image pickup region of the line sensor nearly in the center of the image pickup region of the video camera, the strobe light may be emitted while the particle is present in the image pickup region of the video camera, so that the image of the intended particle may be obtained.

Furthermore, by using the apparatus of the present invention, the light from the excitation light source 10 does not directly enter the video camera 50, and the fluorescence from the particle is sufficiently weak as compared with the strobe light, so that there is no effect on the color image of the particle. As a result, advantageously, the excitation light waveform may be selected freely. The other construction and action (function) are the same as in Embodiment 1.

Being thus constructed, the present invention brings about the following effects.

(1) Since the sample liquid flow in the apparatus of the present invention is flat, many particles can pass per unit time, and the number of particles to be measured may be increased. Moreover, since the sample liquid flat flow is irradiated with fluorescent excitation light from the narrow side, the fluorescent excitation light may be irradiated without loss. Hence, the intensity of the irradiated fluorescent excitation light is strong and uniform, and an intense fluorescence without variance (dispersion) among particles may be obtained.

(2) Unlike the prior art, a long elliptical form of light is not needed, and the apparatus may be simplified. The structure is further simplified because any special element for making the light uniform is not used. There is no annoyance by adjustment of the optical axis.

(3) Side fluorescence and, side scattering light adjusted in focus with the sample liquid flat flow can be detected.

(4) Having an image sensor, morphological information of the particles can be obtained by this image sensor.

(5) Since the irradiation direction of fluorescent excitation light, detecting direction of fluorescence, and image pickup direction of particle image are all different, the direct light of the excitation light does not get into the image pickup means, and fluorescence detection and particle image picking-up may be achieved without the effects of excitation light.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the present invention as defied in the appended claims.

What is claimed is:

1. An apparatus for analyzing particles of a sample liquid, which is enveloped with a sheath liquid, wherein the flow of sample liquid is a flat flow, the apparatus comprising:

a light source for irradiating the sample liquid flat flow with light;

a photo detector for detecting the light emitted from the sample liquid flat flow;

a signal processor for receiving and processing signals from the photo detector; and a condenser lens disposed between the sample liquid flat flow and said light source, the light from said light source passing through the condenser lens, wherein the sample liquid flat flow has a narrower side and a broader side, and wherein the light from said light source is directed to said narrower side, thereby making the light intensity distribution in a detecting region uniform.

2. An apparatus for analyzing particles as claimed in claim 1, wherein said photo detector is designed to detect fluorescence.

3. An apparatus for analyzing particles as claimed in claim 1, wherein said photo detector is designed to detect scattered light.

4. An apparatus for analyzing particles as claimed in claim 1, further comprising:

a second light source for irradiating the sample liquid flat flow with a second light in the direction of said broader side of the sample liquid flat flow; and a one-dimensional image sensor for imaging at least one of the transmitted light images and scattered light images by the second light from the sample liquid flat flow.

5. An apparatus for analyzing particles of a sample liquid, which is enveloped with a sheath liquid, wherein the flow of sample liquid is a flat flow having a narrower side and a broader side, the apparatus comprising:

a light source for irradiating the sample liquid flat flow with light;

a photo detector for detecting the light emitted from the sample liquid flat flow;

a signal processor for receiving and processing signals from the photo detector;

a second light source for irradiating the sample liquid flat flow with a second light in the direction of said broader side of the sample liquid flat flow;

a one-dimensional image sensor for imaging at least one of the transmitted light images and scattered light images by the second light from the sample liquid flat flow;

a third light source for irradiating the sample liquid flat flow with a pulse light in the direction of said broader side of the sample liquid flat flow;

a two-dimensional image sensor for picking up the particle images by the pulse light passing through the sample liquid flat flow; and a signal processor for controlling the radiation of the third light source on the basis of a signal from the one-dimensional image sensor.

* * * * *